United States Patent [19]

Katkocin et al.

[11] Patent Number: 4,628,028

[45] Date of Patent: Dec. 9, 1986

[54] NOVEL THERMOSTABLE PULLULANASE ENZYME AND METHOD FOR ITS PRODUCTION

[75] Inventors: Dennis M. Katkocin, Danbury, Conn.; Nancy W. Zeman, Sleepy Hollow; Shiow-Shong Yang, Downers Grove, both of Ill.

[73] Assignee: CPC International Inc., Englewood Cliffs, N.J.

[21] Appl. No.: 737,309

[22] Filed: May 23, 1985

[51] Int. Cl.[4] .................. C12P 19/22; C12P 19/16; C12N 9/44; C12R 1/01

[52] U.S. Cl. .................................. 435/95; 435/98; 435/210; 435/822; 435/801

[58] Field of Search ................... 435/210, 98, 95

[56] References Cited

U.S. PATENT DOCUMENTS

| | | | |
|---|---|---|---|
| 3,535,123 | 10/1970 | Heady | 435/98 X |
| 3,565,765 | 2/1971 | Heady et al. | 435/210 X |
| 3,838,006 | 9/1974 | Hijiya et al. | 435/98 X |
| 3,897,305 | 7/1975 | Hurst | 435/210 X |
| 3,963,575 | 6/1976 | Bulich | 435/98 |
| 3,992,261 | 11/1976 | Takasaki et al. | 435/98 X |
| 4,011,139 | 3/1977 | Horwath et al. | 435/210 |
| 4,016,038 | 4/1977 | Sugimoto et al. | 435/98 X |

FOREIGN PATENT DOCUMENTS 2097405 11/1982 United Kingdom .

OTHER PUBLICATIONS

American Type Culture Collection Catalogue of Strains I, 15th Edition, 1982 p. 233.
Zeikus, et al, *Arch. Microbiol.*, 122, 41–48 (1979).

*Primary Examiner*—Lionel M. Shapiro
*Attorney, Agent, or Firm*—Stanley M. Parmerter

[57] ABSTRACT

This invention relates to a pullulanase enzyme exhibiting thermostability at a pH of about 5 which is derived from thermophilic, obligately anaerobic bacterium. *T. brockii*, and to a process for its production. The pullulanase is useful for preparation of maltotriose and for conversion of starch to maltose syrups.

8 Claims, No Drawings

NOVEL THERMOSTABLE PULLULANASE ENZYME AND METHOD FOR ITS PRODUCTION

FIELD OF THE INVENTION

This invention relates to a novel enzyme useful for the hydrolysis of certain carbohydrates and to a method for its production by the thermophilic anaerobe, *Thermoanaerobium brockii* (hereafter referred to as *T. brockii*), in an anaerobic fermentation.

BACKGROUND OF THE INVENTION

A number of high molecular weight carbohydrates are polymers of glucose in which the glucose units are joined by either alpha-1,6-glucosidic linkages or alpha-1,4-glucosidic linkages. It is of considerable industrial importance to be able to cleave these linkages thereby breaking the large carbohydrate molecules into smaller molecules which are more useful in various applications. The breaking of the glucosidic linkages is frequently carried out by enzymes which ar produced by microorganisms.

One group of enzymes known as alpha-amylases cleave the alpha-1,4-glucosidic linkages. The alpha-amylase enzymes are produced by such organisms as *Bacillus licheniformis* and *Bacillus stearothermophilus*. Such enzymes generally do not cleave the alpha-1,6-glucosidic linkages.

Another class of enzymes, sometimes referred to as glucoamylases, are capable of cleaving both alpha-1,6- and alpha-1,4-glucosidic linkages. These enzymes remove one glucose unit at a time from the nonreducing end of the large carbohydrate molecule. While they are capable of hydrolyzing certain alpha-1,6-glucosidic linkages, they hydrolyze the alpha-1,4-glucosidic linkages much more rapidly.

Other enzymes which hydrolyze certain alpha-1,6-linkages are classified as pullulanases. These enzymes are capable of hydrolyzing the alpha-1,6-linkages in the polysaccharide, pullulan, to give the trisaccharide, maltotriose. They do not hydrolyze the alpha-1,4-linkages in pullulan. The first pullulanase described was an extracellular enzyme produced by *Klebsiella pneumoniae* (*Aerobacter aerogenes*). References to this enzyme and other enzymes capable of hydrolyzing alpha-1,6-linkages are given in U.S. Pat. Nos. 3,897,305 and 3,992,261. These enzymes are thermolabile and cannot be used at temperatures much above 50° C. A pullulanase enzyme produced by the bacterium, *Bacillus acidopullulyticus*, is described in British Patent No. 2,097,405. This pullulanase is sufficiently thermostable to be employed at 60° C. These enzymes, as well as all previously-known pullulanases, have been obtained from aerobic microorganisms.

We have now discovered a novel pullulanase enzyme which has greater thermostability than any of the reported pullulanases and which is produced by the anaerobic microorganism, *T. brockii*.

SUMMARY OF THE INVENTION

In accordance with the invention, there is provided a thermostable pullulanase enzyme preparation derived from a *T. brockii* microorganism. This enzyme is capable of retaining at least about 50% of its pullulan-hydrolyzing activity when held at 70° C. in an aqueous solution at pH 5.0 for 100 minutes.

Also provided, in accordance with this invention, is a process for producing a pullulanase enzyme which comprises selecting a *T. brockii* microorganism, culturing cells of the selected microorganism in a nutrient medium under anaerobic conditions and then isolating the pullulanase enzyme from the medium.

Further, in accordance with this invention, there is provided a process for converting starch to syrups containing maltose. This process comprises saccharification of starch or starch hydrolyzate with a beta-amylase and an effective amount of the pullulanase enzyme preparation of this invention.

In addition, in accordance with this invention, there is provided a process for the preparation of maltotriose. This process comprises hydrolyzing pullulan with an effective amount of the pullulanase enzyme preparation of this invention.

DETAILED DESCRIPTION OF THE INVENTION

The pullulanase of this invention is produced by the anaerobic thermophilic bacterium, *T. brockii*. Strains of this microorganism have been isolated from hot springs in Yellowstone National Park by Dr. J. G. Zeikus and his co-workers at the University of Wisconsin. They are gram-positive, asporogenous, thermophilic, obligately anaerobic bacteria. Strains of the microorganism are more fully described by Zeikus, et al, *Arch. Microbiol.*, 122, 41–48 (1979). The type strain of this microorganism is freely available to the public from the American Type Culture Collection, Rockville, Md., as ATCC No. 33075.

Cells of the microorganism used for the preparation of the pullulanase enzyme of this invention are grown under anaerobic conditions in a medium which contains a starch or maltodextrin as the carbohydrate source, cottonseed meal, yeast extract plus vitamin and mineral solutions. The presence of nicotinic acid, D-pantothenic acid and magnesium sulfate increases the amount of pullulanase formed, while glucose in the medium inhibits the formation of pullulanase. The optimum pH of the fermentation medium for the production of pullulanase is about 7.

The pullulanase produced by the microorganism was excreted into the fermentation medium. This indicates that the pullulanase is an extracellular enzyme.

The pullulanase enzyme was purified by removing the cells from the fermentation medium followed by precipitation of extraneous matter with calcium chloride. The enzyme solution was concentrated by ultrafiltration, separated by ammonium sulfate precipitation, and further purified by column chromatography using various adsorbents. The enzyme was purified 1100-fold over the crude extract. However, the purified enzyme still showed one major and seven minor protein bands on polyacrylamide gel electrophoresis in the absence of SDS (sodium dodecylsulfate). The major band and two minor bands with lower mobility than the major one exhibited pullulanase activity.

In the following descriptions of the preparation and properties of the pullulanase enzyme, all references to parts and percentages are by weight, unless expressly indicated to be otherwise.

Pullulanase Assay

To 0.40 ml of 2.5% pullulan solution and 0.10 ml of 0.5 M sodium acetate buffer solution at pH 5.0 is added from 0.01 to 0.10 ml of the enzyme solution and sufficient water to give a final volume of 1.0 ml. The solution is incubated at 60° C. for 30 minutes before 1 ml of 1 M Na$_2$CO$_3$ solution is added to stop enzyme action. The reducing sugar released is determined by adding 2 ml of an alkaline K$_3$Fe(CN)$_6$ solution (0.36 mM) to the reaction mixture. The mixture is boiled for exactly 5 minutes and absorbance at 373 nm is measured. Maltose is used as a standard to calibrate the reducing sugar. It is noted that 1 μmole of reducing sugar equals a decrease in absorbance of 0.825.

One unit of pullulanase enzyme activity is defined as the amount of enzym which under standard conditions (60° C. and pH 5.0) hydrolyzes pullulan at a rate to form 1 μmole of maltotriose per minute.

The polysaccharide pullulan, which is a polymer of maltotriose units connected to each other by alpha-1,6-linkages, can be obtained from *Aureobasidium pullulans* (*Pullularia pullulans*) by the procedure of Ueda, et al, *Applied Microbiology*, 11, 211–215 (1963).

Preparation of Pullulanase

Extracellular pullulanase enzyme preparations were prepared from the type strain of *T. brockii*, ATCC No. 33075, obtained from the American Type Culture Collection, Rockville, Md.

Medium preparation and the cultivation of samples were carried out using standard anaerobic techniques as described by Hungate, R. E., "A Roll Tube Method for Cultivation of Strict Anaerobes", in *Methods in Microbiology*, edited by J. R. Norris and D. W. Ribbons, Vol. 3B, Academic Press, New York, 1969, pp. 117–132, and by Miller and Wolin, *Applied Microbiology*, 27, 985 (1974).

The medium used to produce seed and to maintain the stock culture of the organism had the following composition:

| Seed Medium | Percent |
| --- | --- |
| Starch Hydrolyzate[a] | 2 |
| PROFLO[b] | 2 |
| PRYMEX[c] | 1 |
| MnCl$_2$.2H$_2$O | 0.01 |
| KH$_2$PO$_4$ | 0.15 |

[a] A 10 dextrose equivalent (D.E.) hydrolyzate prepared by the partial hydrolysis of waxy maize starch with alpha-amylase enzyme.
[b] A cottonseed meal available from Traders Oil Mill Company, Fort Worth, Texas.
[c] A yeast extract available from Amber Laboratories, Milwaukee, Wisconsin.

Viable cells could be maintained in the seed medium at room temperature for indefinite periods of time. In order to grow the microorganism for production of enzyme, sterile seed medium was inoculated with cells and incubated at 70° C. under anaerobic conditions for approximately 30 hours. This produced rapidly-growing cells which were used to inoculate a fermentor. The volume of inoculum was about 5% of the volume of the growth medium in the fermentor. This medium had the following composition:

| Growth Medium | Percent |
| --- | --- |
| Starch Hydrolyzate | 4.5 |
| PROFLO | 7 |
| PRYMEX | 2 |
| MgSO$_4$.7H$_2$O | 0.3 |
| CaCl$_2$.2H$_2$O | 0.3 |
| KH$_2$PO$_4$ | 0.3 |
| K$_2$HPO$_4$ | 0.5 |
| (NH$_4$)$_2$HPO$_4$ | 0.3 |

| Growth Medium -continued | Percent |
| --- | --- |
| Nicotinic Acid | 0.05 |

The pH of the medium was adjusted to 7 and production runs were made in 16-liter and 40-liter fermentors. After 44 hours, the yield of extracellular pullulanase enzyme was 0.9 to 1.2 units per ml of fermentation broth.

Purification of the Enzyme

The fermentation broth (about 12 liters) was first filtered through glass wool to remove a gummy insoluble substance. Cells were then removed from the filtrate by means of a Sharples continuous scroll centrifuge, Model 741-24/8R4 (Sharples Corp., Philadelphia, Pa.), operating at 20,000 rpm. To the clear supernatant was added sufficient calcium chloride to give a final concentration of about 3% w/v and the mixture was stirred for 10 minutes. The bulky precipitate was removed by filtration and discarded.

Adjustment of the pH of the filtrate to 6 with concentrated ammonium hydroxide gave a second precipitate which was also removed and discarded. The pink-colored filtrate wa concentrated to about 1 liter using an Amicon hollow-fiber (Model DC2) concentrator, available from the Amicon Corp., Danvers, Mass. Ammonium sulfate was added to the clarified solution to give a concentration of about 30% of saturation and the mixture was stirred for 1 hour. The precipitate was removed by centrifugation (6000×g, for 20 minutes) before sufficient ammonium sulfate was added to the supernatant to give a solution containing 80% of the amount needed for saturation with this salt. The mixture was stirred overnight at 4° C. before the precipitate was collected by centrifugation.

The precipitate was dissolved in a small volume of 25 mM acetate buffer at pH 6. This enzyme solution was dialyzed against 20 liters of the same buffer at 4° C. but with three changes of the buffer in 24 hours. The dialyzed solution was centrifuged and the supernatant was adsorbed on a column of DEAE-cellulose (Whatman DE-52) which had been equilibrated with a pH 6 acetate buffer. The column containin the adsorbed enzyme was washed with 400 ml of buffer before it was eluted with 1000 ml of buffer containing 100 mM NaCl. Finally, the material was eluted with 200 ml of 400 m NaCl.

Fractions from the 400-mM NaCl eluate, which were rich in enzymatic activity, were combined and concentrated to 20 ml using an Amicon ultrafiltration cell fitted with a YM 10 membrane. The dark-brown retentate was applied to a column of Ultrogel AcA 34 which had been equilibrated with 2000 ml of sodium acetate buffer (50 mM, pH 6), containing 100 mM NaCl. The material was eluted from the column using the sodium acetate buffer containing 100 mM NaCl at a flow rate of 16 ml per hour. Five-ml fractions of effluent were collected.

Fractions rich in enzymatic activity were combined, diluted threefold with water and adsorbed on DEAE-SEPHAROSE column which had previously been equilibrated with 25 mM acetate buffer, pH 6. After washing with 150 ml of the acetate buffer, the column was eluted with a 600-ml linear gradient of NaCl (50 mM to 400 mM in the acetate buffer). The flow rate was 36 ml per hour and fractions of 6 ml volume were collected. Fractions containing the enzyme activity were pooled and dialyzed against 1000 ml of mM acetate buffer, pH 4.5 at 4° C. with two changes of the buffer overnight.

The dialyzed enzyme solution was centrifuged and the yellow supernatant was applied to a column of CM-SEPHAROSE which had been equilibrated with 25 mM acetate buffer, pH 4.5. A yellow, inactive substance was held on the top of the column and the enzyme was recovered in the colorless unadsorbed fraction. The enzyme solution was concentrated to 2 ml and applied to a column of Ultrogel AcA 34 which had been equilibrated with 25 mM acetate buffer containing 100 mM NaCl. The material was eluted at a rate of 8 ml per hour with 2-ml fractions being collected. Fractions high in enzymatic activity were pooled and stored at 4° C. for use in determining properties of the enzyme. The molecular weight of the enzyme was estimated by rate of flow through the column using the method for estimating molecular weights of proteins by gel filtration described by Andrews, *Biochem. J.*, 91, 222-233 (1964). This method gave an approximate molecular weight of 90,000 for the enzyme.

Ultrogel AcA 34 was obtained from LKB Instruments Inc., Gaithersburg, Md. DEAE-SEPHAROSE and CM-SEPHAROSE were obtained from Pharmacia Fine Chemicals, Piscataway, N.J. The protein content of the enzyme-containing solution was determined by the method of Lowry, et al, *J. Biol. Chem.*, 193, 265-275 1951), using

TABLE I

PURIFICATION OF T. BROCKII PULLULANASE

| Procedure | Volume (ml) | Units per ml | Units per mg Protein | Yield (%) |
|---|---|---|---|---|
| Fermentation Broth | 12,170 | 0.23 | 0.0284 | — |
| CaCl$_2$ Treatment | 12,120 | 0.22 | 0.0353 | 95 |
| Ultrafiltration | 1,080 | 1.88 | 0.0647 | 73 |
| Ammonium Sulfate Precipitate (30-80% saturation) | 770 | 2.34 | 0.1032 | 65 |
| DE-52 Column (4 × 16 cm) | 520 | 1.44 | 0.7590 | 27 |
| Ultrogel AcA 34 Column (2.5 × 85 cm) | 162 | 3.07 | 1.004 | 18 |
| DEAE-SEPHAROSE Column (2.2 × 18 cm) | 106 | 2.06 | 2.064 | 8 |
| CM-SEPHAROSE Column (2.2 × 14 cm) | 61 | 2.47 | 10.152 | 5 |
| Ultrogel AcA 34 Column (1.8 × 100 cm) | 38 | 3.07 | 31.649 | 4 |

Thermostability of the Enzyme

The thermostability of the T. brockii pullulanase was examined by incubation in 50 mM acetate buffer (pH 5) in the absence of substrate at 70° C. The enzyme solution was prepared to contain one pullulanase unit per ml. Bovine serum albumin was added to the dilute solution to give a protein concentration of about 230 μg/ml. Samples which had been incubated at 20, 40, 80, and 160 minutes were then assayed at pH 5 and 60° C. for residual enzymatic activity. The enzyme showed a half-life of 149 minutes under these conditions. The debranching enzyme, PROMOZYME (Novo Labs., Wilton, Conn.), from *Bacillus acidopullulyticus* (British Patent No. 2,097,405), was tested under the same conditions. It lost all of its enzymatic activity in less than 5 minutes. This demonstrates the superior thermostability of the present enzyme over the most thermostable pullulanase enzyme previously disclosed.

Temperature Optimum for the Enzyme

The effect of the reaction temperature on the purified enzyme was determined by performing the standard (pH 5) pullulanase assay at various temperatures. At this pH the temperature optimum of the enzyme was found to be 85° C.

pH Effect on the Enzyme

The pullulanase enzyme activity was analyzed by the standard procedure except that the pH of the substrate was varied from 3.5 to 10 using 100-mM buffer solutions of the following compositions: sodium acetate (pH 3.5 to 6), potassium phosphate (pH 6.5 to 7), Tris acetate (pH 7.5 to 8.5) and glycine NaOH (pH 9 to 10). The enzyme showed the maximum activity at pH 5 and about 35% of its maximum activity at pH 4 and 6.5. When the enzyme was incubated at various pHs and 60° C. for 47 hours before the residual pullulanase activity was determined at pH 5 and 60° C. the enzyme retained over 90% of its original activity at all pHs between 4.5 and 9.0.

Substrate Specificity of the Enzyme

The enzyme hydrolyzes exclusively the 1,6-linkages in pullulan to give maltotriose as the final hydrolysis product. High performance liquid chromatography (HPLC) analysis of partial digests of pullulan using a size exclusion column shows that the enzyme cleaves the pullulan molecule in a random manner. None of the 1,4-linkages in pullulan are attacked by this enzyme. A 50-mM acetate buffer solution containing 50 mg/ml pullulan and 1 unit/ml of the pullulanase enzyme was incubated at 60° C. for 24 hours. Analysis by HPLC showed that the product contained 83.6% maltotriose plus small amounts of oligomers containing 2 and 3 maltotriose units. Also present was a small amount of maltotriose higher molecular weight material.

The enzyme does not hydrolyze panose, maltotriose, isomaltose, or the dextran from *Leuconostoc mesenteroides* which contains principally 1,6-linkages between the glucose units.

The enzyme hydrolyzed oyster glycogen (Sigma Chemical Co., St. Louis, Mo.) and Lintner starch (J. T. Baker Chemical Co., Phillipsburg, N.J.) as shown by production of reducing sugars. Initial rates of hydrolysis of these carbohydrates was about one-fifth the initial rate of hydrolysis of pullulan.

The Lintner starch and the product obtained by its hydrolysis with the pullulanase were analyzed by high resolution $^{13}$C nuclear magnetic resonance spectroscopy. Both the starch and its hydrolyzate contained about 4.7% of the glucose units joined by 1,6-linkages. This indicates that the pullulanase hydrolyzed essentially none of the 1,6-linkages in the starch. On the other hand, the enzyme hydrolyzed about 17% of the 1,4-linkages in the starch. This clearly distinguishes this enzyme from previously-known pullulanases which hydrolyze 1,6-linkages rather than 1,4-linkages in starch. Available evidence indicates that the ability of the present pullulanase to hydrolyze 1,4-linkages in starch is inherent in the enzyme and is not due to contaminating alpha-amylase enzyme.

Pullulanase Produced by *Bacillus subtilis* Containing Recombinant DNA

A strain of *Bacillus subtilis* (hereafter *B. subtilis*) containing a plasmid having the gene coding for the *T. brockii* pullulanase enzyme was used to prepare the enzyme. This strain and its use to prepare the enzyme are disclosed in a copending patent application Ser. No. 737,312, titled: "Plasmids Containing a Gene Coding for a Thermostable Pullulanase and Pullulanase-Producing Strains of *Escherichia coli* and *Bacillus subtilis* Containing the Plasmids", filed concurrently with this application, the disclosure of which is incorporated herein by reference in its entirety.

To 1520 ml of the *B. subtilis* fermentation broth containing 1292 units of pullulanase enzyme was added 45.6 g of $CaCl_2$ and the mixture was stirred for 10 minutes. The bulky precipitate was removed by centrifugation at 4800×g for 20 minutes. Glacial acetic acid was added to the supernatant to reduce the pH to 5.

The enzyme was adsorbed from the solution on granular corn starch (Code 3005, CPC International Inc., Englewood Cliffs, N.J.). This was accomplished by stirring the solution with 125 g of granular corn starch which had previously been equilibrated with 50 mM sodium acetate buffer at pH 5. The starch containing the enzyme was removed by filtration and washed twice with 600 ml of cold acetate buffer. The enzyme was then desorbed from the starch by heating the starch with 400 ml of the acetate buffer at 60° C. for 1 hour with stirring. The extraction step was repeated with two additional 250-ml portions of acetate buffer and the extracts were combined for use in the next purification step.

Solid ammonium sulfate (153 g) was added to the enzyme solution. No precipitate formed. The clear solution was applied to a 1.6×12-cm column of Octyl-SEPHAROSE CL-4B (Sigma Chemical Co.) previously equilibrated with a solution containing 30% of saturation of ammonium sulfate in potassium phosphate buffer (50 mM, pH 6.5). The column was washed with 180 ml of the ammonium sulfate-phosphate buffer solution and then eluted stepwise with decreasing concentrations of ammonium sulfate (20%, 10%, and 0% of saturation) in the phosphate buffer. The 10% and 0% ammonium sulfate eluates both contained pullulanase activity. They were collected separately and each concentrated to about 2 ml in a concentrator fitted with a YM 10 membrane.

Each separate enzyme solution was adsorbed on a 1.6×100-cm Ultrogel AcA 44 column which had been equilibrated with 50 mM sodium acetate buffer (pH 5) containing 100 mM NaCl and 0.02% sodium azide. The material was eluted with the buffer solution which had been used to equilibrate the column, and fractions showing pullulanase activity were combined. The results of the purification are summarized in Table II which shows that the two purified enzymes possess pullulanase specific activities of 45 and 50 units per mg of protein which correspond to purifications of 850- and 950-fold, respectively.

TABLE II
PURIFICATION OF CLONED T. BROCKII PULLULANASE ENZYME

| Procedure | Volume (ml) | Units per ml | Units per mg Protein | Yield (%) |
|---|---|---|---|---|
| Fermentation Broth | 1520 | 0.850 | 0.053 | — |
| $CaCl_2$ Treatment | 1520 | 0.816 | 0.495 | 95 |
| Starch Affinity | 870 | 0.727 | 1.605 | 49 |
| Octyl-SEPHAROSE Column (1.6 × 12 cm) | | | | |
| Cloned Enzyme - No. 1 | 59 | 6.739 | 24.068 | 31 |
| Cloned Enzyme - No. 2 | 220 | 0.925 | 5.506 | 16 |
| Ultrogel AcA 44 Column (1.8 × 100 cm) | | | | |
| Cloned Enzyme - No. 1 | 43 | 7.879 | 45.543 | 26 |
| Cloned Enzyme - No. 2 | 32 | 2.828 | 50.500 | 7 |

Polyacrylamide gel electrophoresis showed that the purified enzymes still contained minor amounts of protein contaminants. Furthermore, two major protein bands with equal intensity were revealed for Enzyme No. 2. By comparing mobilities of the enzymes with that of marker proteins, molecular weights of 125,000 were estimated for Enzyme No. 1 and of 110,000 and 95,000 for the two proteins of Enzyme No. 2. The three different proteins appeared to have the same pullulanase activity.

A sample of the pullulanase enzyme solution, obtained after desorption from granular starch, was subjected to polyacrylamide gel electrophoresis and stained by the periodic acid-Schiff procedure (Clemetson, et al, *Biochim. Biophys. Acta*, 553, 11–24 (1979)). No glycoprotein band was detected. In contrast, the natural *T. brockii* pullulanase gave a positive glycoprotein test by this procedure.

A sample of the pullulanase enzyme solution, obtained after desorption from granular starch, was further purified by gel filtration. It was tested for thermostability using the test described for the enzyme produced by native *T. brockii*. In this case, bovine serum albumin was added to the solution to give a protein concentration of 200 µg per ml. The half-life of the pullulanase at 70° C. and pH 5 was about 109 minutes. The half-life of the enzyme produced by *T. brockii* when tested under the same conditions was about 241 minutes. This indicates that the pullulanase produced by *B. subtilis* containing recombinant DNA is somewhat less thermostable than the corresponding enzyme produced by *T. brockii*.

A sample of the pullulanase enzyme solution, prepared as in the preceding paragraph, was used to make a syrup of high maltose content. To a 2% solution of waxy maize starch in 50 mM acetate buffer at pH 5 was added soybean beta-amylase powder (10 mg per g starch) and pullulanase enzyme (2 units per g starch) and the mixture was incubated at 60° C. for 72 hours. Analysis by HPLC indicated that the resulting syrup contained about 80% maltose on a dry solids basis. In a comparable experiment in which no pullulanase enzyme was added, the resulting syrup contained only about 57% maltose.

The production of maltose using the enzyme to treat a corn starch hydrolyzate was also investigated. To a 30% (w/v) solution of Maltrin M-100, a 10 D.E. starch hydrolyzate, available from the Grain Processing Co., Muscatine, Iowa, was added 0.1 g of the soybean beta-amylase per gram of starch and 4 units of the pullulanase enzyme per gram of starch. The pH of the mixture was adjusted to 5 before it was incubated at 60° C. for 96 hours. HPLC analysis of the resulting syrup indicated that it contained about 67% maltose on a dry solids basis. A control run using only beta-amylase gave a syrup containing about 58% maltose on a dry solids basis. This indicates that the pullulanase enzyme of this invention also is useful for producing high maltose syrups in concentrated solutions.

Thus, there has been provided, in accordance with this invention, a thermostable pullulanase enzyme and a process for its preparation. While the invention has been described in conjunction with specific embodiments thereof, it is evident that many alternatives, modifications, and variations will be apparent to those skilled in the art in light of the foregoing description. Accordingly, it is intended to include all such alternatives, modifications, and variations as set forth within the spirit and scope of the appended claims.

what is claimed is:

1. A thermostable pullulanase enzyme preparation derived from a *Thermoanaerobium brockii* microorganism, said enzyme being capable of retaining at least about 50% of its pullulan-hydrolyzing activity when held at 70° C. in an aqueous solution in the absence of substrate at pH 5.0 for 100 minutes.

2. The pullulanase enzyme preparation of claim 1 having a maximum pullulan-hydrolyzing activity at a pH of about 5.0 when measured at 60° C.

3. The pullulanase enzyme preparation of claim 1 having a maximum pullulan-hydrolyzing activity at pH 5.0 at a temperature of about 85° C.

4. The pullulanase enzyme preparation of claim 1 wherein the *Thermoanaerobium brockii* microorganism is strain ATCC No. 33075, or a variant or mutant thereof.

5. A process for producing a pullulanase enzyme which comprises selecting a *Thermoanaerobium brockii* microorganism, culturing cells of the selected microorganism in a nutrient medium under anaerobic conditions and then isolating the pullulanase enzyme from the medium.

6. The process of claim 5 wherein the *Thermoanaerobium brockii* microorganism is strain ATCC No. 33075, or a variant or mutant thereof.

7. A process for converting starch into syrups containing maltose which process comprises saccharification of starch or starch hydrolyzate with a beta-amylase and an effective amount of the pullulanase enzyme preparation of claim 1.

8. A process for the preparation of maltotriose which comprises hydrolyzing pullulan with an effective amount of the pullulanase enzyme preparation of claim 1.

* * * * *

UNITED STATES PATENT AND TRADEMARK OFFICE
CERTIFICATE OF CORRECTION

PATENT NO. : 4,628,028
DATED : December 9, 1986
INVENTOR(S) : Dennis M. Katkocin, et al It is certified that error appears in the above-identified patent and that said Letters Patent are hereby corrected as shown below:

Column 1, line 21, "ar" should read --are--.
Column 3, line 11, "enzym" should read --enzyme--.
Column 4, line 28, "wa" should read --was--.
Column 4, line 47, "containin" should read --containing--.
Column 4, line 50, "400 m" should read --400 mM--.
Column 5, line 31, after "using" insert --bovine serum albumin as a standard. The results of the purification procedure for the enzyme material are given in Table I.--.
Column 6, line 8, after "pH" insert a comma --,--.
Column 6, line 23, after "60° C." insert a comma --,--.

Signed and Sealed this

Twenty-first Day of April, 1987

Attest:

DONALD J. QUIGG

Attesting Officer

Commissioner of Patents and Trademarks